United States Patent [19]

Reynolds et al.

[11] E Patent Number: Re. 33,360

[45] Reissued Date of Patent: Oct. 2, 1990

[54] DISPOSABLE TRANSDUCER APPARATUS FOR AN ELECTROMANOMETRY SYSTEM

[75] Inventors: Gordon S. Reynolds, Bountiful; Robert J. Todd, Salt Lake City, both of Utah; Edward J. Russell, San Jose, Calif.

[73] Assignee: Abbott Laboratories, Abbott Park, Ill.

[21] Appl. No.: 131,161

[22] Filed: Dec. 10, 1987

Related U.S. Patent Documents

Reissue of:

[64] Patent No.: 4,557,269
Issued: Dec. 10, 1985
Appl. No.: 506,753
Filed: Jun. 22, 1983

[51] Int. Cl.[5] ..... A61B 5/02

[52] U.S. Cl. ..... 128/675; 128/748; 73/740

[58] Field of Search ..... 128/672–675, 128/748; 73/708, 720–721, 725–727, 4 R, 740

[56] References Cited

U.S. PATENT DOCUMENTS

| | | | |
|---|---|---|---|
| 3,482,197 | 12/1969 | Kondo et al. | 338/4 |
| 3,592,187 | 7/1971 | Youdin | 128/675 |
| 3,631,850 | 1/1972 | Levasseur | 128/675 |
| 3,648,687 | 3/1972 | Ramsey, III | 128/673 |
| 3,720,201 | 3/1973 | Ramsey, III | 128/748 |
| 3,772,628 | 11/1973 | Underwood et al. | 338/4 |
| 3,817,107 | 6/1974 | Shimada et al. | 73/727 |
| 3,818,765 | 6/1974 | Eriksen | 73/706 |
| 3,831,588 | 8/1974 | Rindner | 128/675 |
| 3,890,842 | 6/1975 | Ramsey, III | 73/731 |
| 3,890,962 | 6/1975 | Ramsey, III | 128/673 |
| 3,922,705 | 11/1975 | Yerman | 357/26 |
| 3,946,724 | 3/1976 | La Balme | 73/706 |
| 3,981,197 | 9/1976 | Lieber et al. | 73/727 |
| 4,023,562 | 5/1977 | Hynecek et al. | 128/748 |
| 4,072,056 | 2/1978 | Lee | 73/706 |
| 4,077,882 | 3/1978 | Gangemi | 128/675 X |
| 4,185,641 | 1/1980 | Minior et al. | 128/675 |
| 4,203,327 | 5/1980 | Singh | 73/721 |
| 4,226,124 | 10/1980 | Kersten | 73/706 |
| 4,237,935 | 12/1980 | Delmonte et al. | 128/675 X |
| 4,252,126 | 2/1981 | Mandl | 128/673 |
| 4,274,423 | 6/1981 | Mizuno et al. | 128/675 |
| 4,314,226 | 2/1982 | Oguro et al. | 73/727 X |
| 4,431,009 | 2/1984 | Marino, Jr. et al. | 128/675 X |

OTHER PUBLICATIONS

Delannois, "Medical & Biological Engineering", vol. 12, No. 3, May 1974, pp. 364–365.

*Primary Examiner*—Angela D. Sykes
*Attorney, Agent, or Firm*—A. Nicholas Trausch, III

[57] ABSTRACT

The disposable transducer includes a small housing constructed of lightweight plastic material. The housing is shaped so as to form a transparent chamber within which is situated a very small piezoresistive strain gauge in the form of a resistive bridge network diffused onto a semiconductor substrate. The semiconductor substrate is electrically isolated by means of a nonconductive gel which partially fills the transparent chamber in which the semiconductor substrate is positioned. The resistive bridge network of the semiconductor substrate is also electrically connected to a plurality of calibration resistors which are separately formed on the semiconductor substrate, making the entire apparatus economically disposable after a single use.

9 Claims, 5 Drawing Sheets

DISPOSABLE TRANSDUCER APPARATUS FOR AN ELECTROMANOMETRY SYSTEM

Matter enclosed in heavy brackets [ ] appears in the original patent but forms no part of this reissue specification; matter printed in italics indicates the additions made by reissue.

BACKGROUND OF THE INVENTION

1. Field of the Invention

The present invention relates to pressure transducers and, more particularly, the present invention is directed to a disposable transducer apparatus for use in an electromanometry system for monitoring and recording hemodynamic pressures.

2. The Prior Art

With the advent of high speed digital computers in the 1950's and 1960's, a number of medical teams throughout the United States began considering the possibility of computerized blood pressure monitoring. Today, computerized blood pressure monitoring systems are frequently used in intensive care facilities to provide around-the-clock computer monitoring of hemodynamic pressures in critically ill heart patients both during and following cardiovascular surgery and the like.

As the heart pumps, the resistance to fluid flow and elasticity of the blood vessels cause a buildup in the arteries of a continuous mean blood pressure having a superimposed fluctuation between a maximum and minimum pressure, known as systolic and diastolic pressures, respectively. It is the function of a computerized blood pressure monitoring system to continuously measure and electronically record measurements of the cyclical blood pressures which occur by virtue of the heart's pumping action.

In order to transform these measurements of cyclical blood pressures into recordable electronic waveforms, a catheter filled with a sterile saline solution is inserted into a patient's artery and is threaded through the artery until the tip of the catheter is located near the heart. In this way, the periodic pulsations of blood are transmitted as mechanical pulses of fluid through the saline-filled catheter. The catheter tubing is connected to a pressure transducer which converts the mechanical pressure pulses through the saline in the catheter into electronic waveforms that may be visually displayed on an oscilloscope screen or on a recording strip chart. These electronic waveforms are subsequently analyzed by a computer to determine a number of quantitative parameters, including heart rate, duration of systole, and systolic, diastolic and means pressures. This information gives the surgeon and other health care personnel a quantitative look at the operation of a patient's heart, and is thus extremely valuable in helping to assess the clinical course of critically ill patients on a continuously updated basis.

The pressure transducers typically used in an electromanometry system are relatively expensive. Thus, in the past the practice has been to resterilize the transducer after using it on a patient so that it could be used anew on other patients. This practice tended to increase the risk of cross-contamination among patients, and also resulted in increased maintenance costs and inconvenience. Moreover, because such transducers are expensive, if one was accidentally damaged or dropped, the expense to the hospital became significant. A further disadvantage of the prior art transducers is their size and weight. Because of these size and weight considerations prior art pressure transducers were mounted on brackets attached to a standard I.V. pole. This separate mounting caused inconvenience and undue complication when setting up the electromanometry system or transporting the patient. The prior art type transducers also require frequent calibration, thus adding to the maintenance costs and inconvenience already present with these devices.

In an effort to reduce the expanse and inconvenience associated with having to resterilize non-disposable transducers after each use, disposable pressure transducer domes have been developed which physically isolate the transducer from the saline solution carried by the catheter tubing. The disposable transducer domes typically consist of a thin plastic membrane which is used to physically separate the diaphragm of the transducer from the saline solution so that the diaphragm is not contaminated by the saline solution, which has been in contact with the patient's blood. Although such disposable transducer domes help to minimize the risk of contamination and also help to reduce the cost associated with resterilization of pressure transducers, the plastic membrane attenuates the mechanical pressures transmitted through the saline solution, with the result that the resulting electronic waveforms are often degraded in quality.

Further efforts to improve the state of the art concerning pressure transducers used in connection with blood pressure monitoring have included efforts to develop smaller, miniaturized versions of the pressure transducer. The smaller, miniaturized pressure transducers, although much reduced in size so that they can be directly supported on the arm of the patient or by the pressure tubing, nevertheless are expensive to construct and are still intended to be reused, thus requiring continued use of disposable transducer domes.

Thus, what is needed in the art is a very small, lightweight transducer which is sufficiently economical in its construction as to be disposable after each use, thus eliminating the need for resterilization techniques and also eliminating the need for using disposable transducer domes.

BRIEF SUMMARY AND OBJECTS OF THE INVENTION

It is a primary object of the present invention to overcome the foregoing disadvantages of those transducers which represent the current state of the art by providing a very small, ultra lightweight pressure transducer which is highly economical to manufacture and which may be disposed of after each single use.

Another important advantage of the present invention is to provide a disposable pressure transducer which may be easily, quickly and accurately calibrated.

Yet another advantage of the present invention is to provide a disposable pressure transducer for monitoring hemodynamic pressures by means of an indwelling, liquid-filled catheter, in which the pressure sensing element of the transducer is electrically isolated from the sterile saline solution contained in the catheter tubing.

Yet another advantage of the present invention is to provide a disposable pressure transducer for monitoring hemodynamic pressures which accurately converts the mechanical pressures transmitted in the form of fluid pulses into changes in electrical resistance which can be detected and transformed into corresponding electronic signals.

Still another advantage of the present invention is to provide a disposable pressure transducer which effectively reduces the risk of cross-contamination by eliminating the need for resterilization techniques, and which also eliminates the need for physical isolation through the use of disposable domes.

These and other advantages and features of the present invention will become more apparent from the following description and claims taken in conjunction with the accompanying drawings.

In accordance with the foregoing objects, the present invention includes a very small, ultra lightweight pressure transducer which is highly economical to manufacture and which may be disposed of after a single use. The disposable pressure transducer is adapted for use in an electromanometry system such as typically used in the case of computerized blood pressure monitoring systems for recording hemodynamic pressures by means of an indwelling catheter inserted into an artery or vein of a patient. The disposable transducer includes a small housing constructed of medical grade plastic material. The housing is shaped so as to form a transparent chamber within which is situated a very small semiconductor substrate. A piezoresistive strain gauge in the form of a resistive bridge network diffused onto the substrate forms the pressure sensitive element which converts the mechanical pressure pulses of fluid into changes in electrical resistance which can be detected and transformed into corresponding electronic signals. The pressure sensing element of the transducer is electrically isolated from the saline solution by means of a nonconductive gel which completely covers the pressure sensing element and accurately transmits the mechanical fluid pulses to the resistive bridge network diffused onto the substrate. The resistive bridge network may also be electrically connected to a plurality of calibration resistors which are separately formed on the disposable semiconductor substrate.

DETAILED DESCRIPTION OF THE PREFERRED EMBODIMENT

Figure 1:
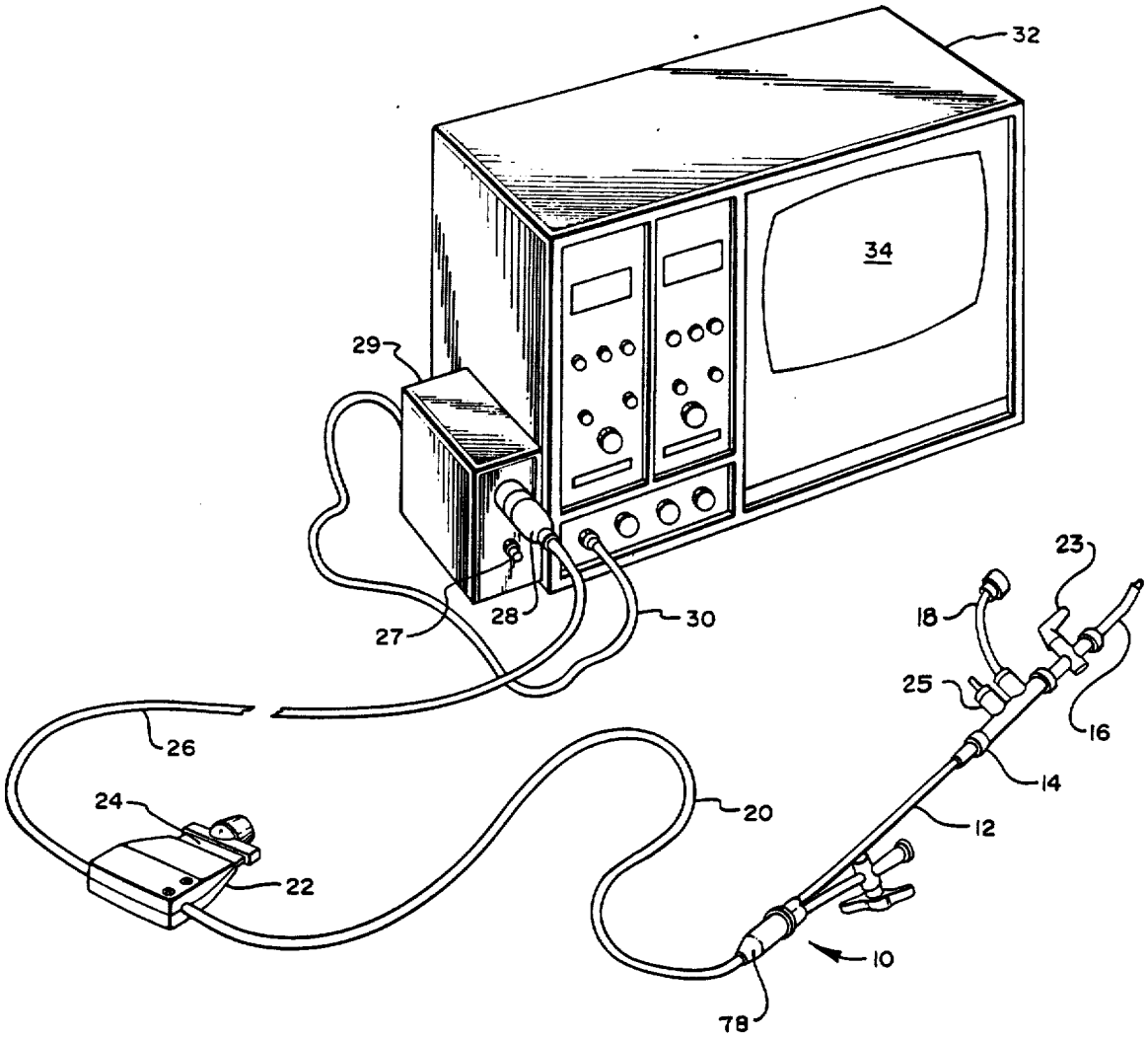
FIG. 1 is a perspective illustration of an electromanometry system used for monitoring hemodynamic pressures, the system incorporating a disposable pressure transducer together with a disposable card used for calibrating the transducer.

While this invention is susceptible of embodiment in many different forms, there is shown in the drawings and will hereinafter be described in detail several specific embodiments with the understanding that the present disclosure is to be considered as an exemplification of the principles of the invention and are not intended to limit the invention to the embodiments illustrated.

Figure 8:
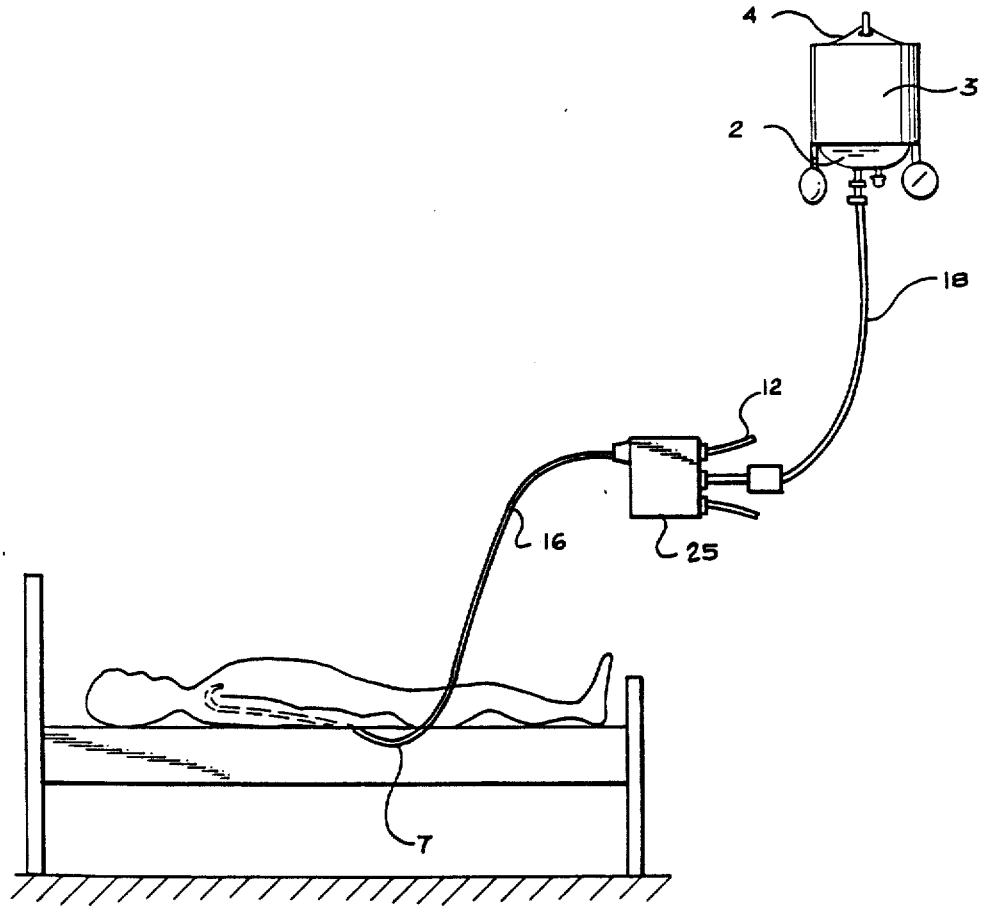
FIG. 8 is a schematic diagram showing a conventional flushing system for use with an electromanometry system.

Referring first to FIG. 1, the small, ultra lightweight disposable pressure transducer apparatus constructed in accordance with the apparatus of the present invention is generally designated as 10. The pressure transducer apparatus 10 is connected at one end through a short length of tubing 12 to a conventional luer lock fitting 14 which in turn connects to the pressure tubing 16 which leads to the catheter 7 (best seen in FIG. 8) which is inserted into the patient. As shown in FIG. 8 a pressurized source of sterile saline solution 2 is typically provided by means of a pressure cuff 3 which surrounds a flexible plastic bag 4 containing the saline solution 2. The bag 4 is connected in parallel to pressure tubing 16 by another length of tubing 18 which leads to the bag 4 of saline solution 2.

As previously indicated, in the case of arterial blood pressure monitoring, the catheter 7 is inserted into the artery of a patient and is then threaded through the artery, preferably to the central vena cava.

Returning to FIG. 1, the other end of the transducer apparatus 10 is connected through a first electrical socket [78] *19* to an electrical cable 20. Cable 20 is connected to a second electrical socket 22, which is adapted to receive a disposable calibration card 24. The calibration card 24 is used to calibrate the transducer apparatus 10, as hereinafter more fully described. From second electrical socket 22, another length of electrical cable 26 is connected through plug 28 to an interface circuit contained in a metal housing 29.

As hereinafter more fully explained, the hemodynamic pressures generated by the pumping action of the heart are transmitted as fluid pulses through the blood carried in the artery and then through the saline solution carried by the catheter 7 as shown in FIG. 8 and the pressure tubing 12 and 16. The hemodynamic pressures in the form of fluid pulses are then transformed by transducer apparatus 10 into corresponding electronic signals which are input through the interface circuit to the monitor 32. The corresponding electronic wave forms are output on the oscilloscope screen 34 of monitor 32 or, in the alternative, they may be output on a recording strip chart (not shown).

Figure 9:
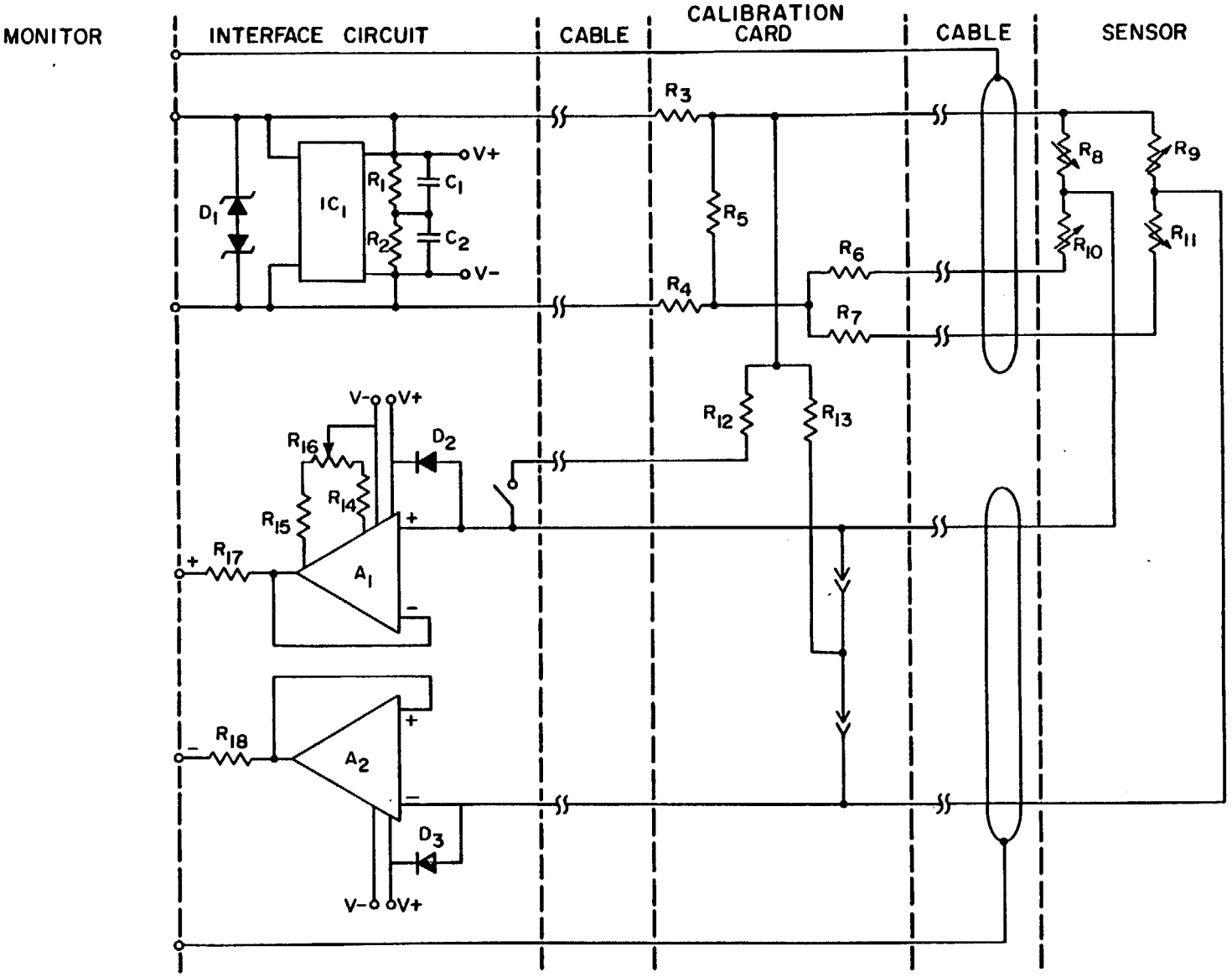
FIG. 9 of the drawings is a schematic diagram showing the calibration resistors and the resistive bridge network of FIG. 5 connected to an interface circuit.

As best seen in FIG. 9, the commonly known in the art, the interface circuit is used for purposes of matching the impedence of the circuit from transducer apparatus 10 through plug 28 with the input circuitry of the monitor 32. The interface circuit is connected through cable 30 to the monitor 32. Monitor 32 is activated by means of switch 27.

Figure 2:
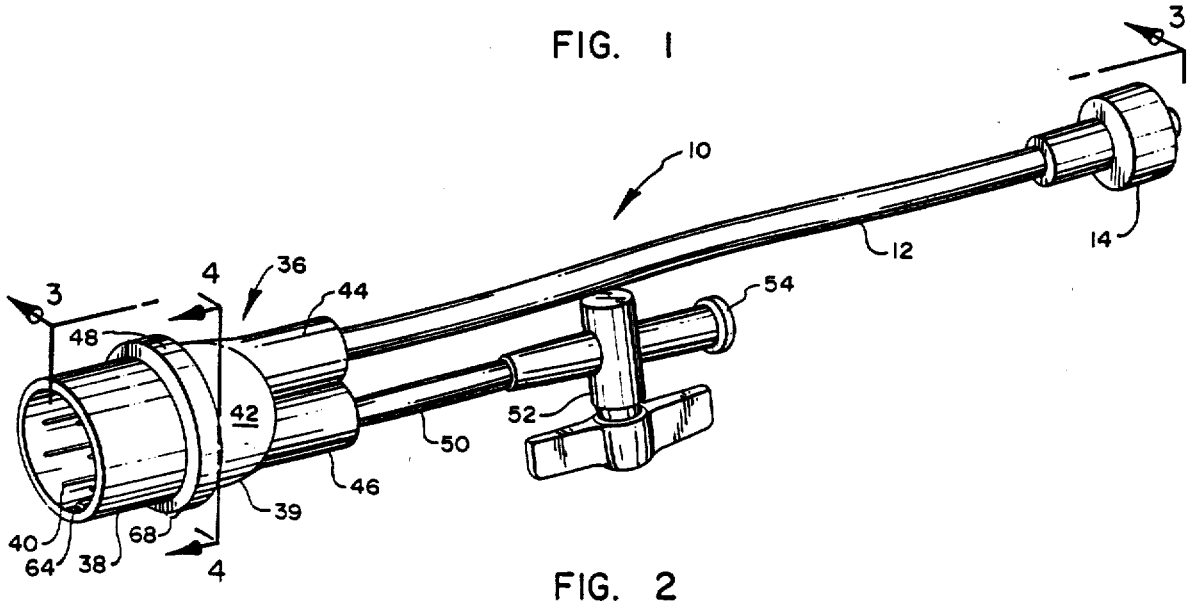
FIG. 2 is an enlarged perspective view illustrating the disposable pressure transducer of the present invention.
Figure 3:
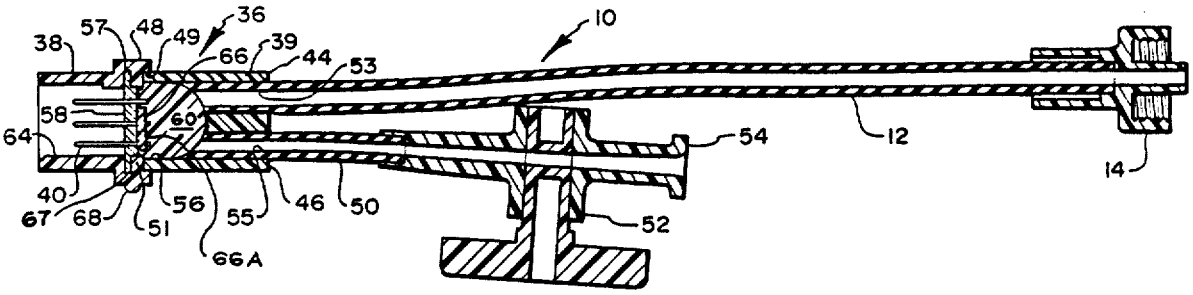
FIG. 3 is a longitudinal sectional view taken along lines 3—3 of the disposable pressure transducer of FIG. 2.

Reference is next made to FIGS. 2 and 3 which show in more detail the specific configuration of one presently preferred embodiment of a disposable pressure transducer apparatus constructed in accordance with the apparatus of the present invention. The illustrations in FIGS. 2 and 3 have been enlarged so that the details of construction may be more clearly seen.

As shown best in FIG. 3, the transducer apparatus 10 includes a housing 36 which consists of two halves 38 and 39. The distal half 38 of housing 36 has a ring 48 which forms an annular recess 49 (see FIG. 4) into which the leading end of the proximal half 39 of housing 36 is secured by solvent bonding or other suitable methods. The ring 48 also has an annular flange 51 which projects inwardly and which provides support for the leading edge of the proximal half 39 of the housing 36.

As shown best in FIGS. 2 and 3, the leading portion of the proximal half 39 of housing 36 is formed in the shape of a hemispherical dome 42. Dome 42 has an interior chamber 56 (see FIG. 3) which is filled during use with the sterile saline solution 2 as hereinafter more fully described. Dome 42 has cylindrical fittings 44 and 46 integrally formed and extending therefrom(see FIG. 2) which are adapted to receive the short lengths of tubing 12 and 50 respectively. As shown best in FIG. 3, the fitting 44 provides an inlet passageway 53 which places the interior chamber 56 of dome 42 in fluid communication with the sterile saline solution carried by tubing 12, which in turn is connected to the pressure tubing 16 and catheter 7 (as shown in FIG. 8) inserted into the patient. The short length of tubing 50 connected through fitting 46 provides an outlet passageway 55 which terminates in a conventional stopcock 52. Thus, when the catheter 7 and pressure tubing 16 are initially filled with a fluid such as the sterile saline solution 2, stopcock 52 is opened so that the sterile saline solution will enter the interior chamber 56 until it is full and air may be expelled through port 54. Interior chamber 56 may thereby be completely filled with fluid in a conventional manner (see FIG. 1) utilizing stopcock 23 and flush device 25 that is attached to a bag 4 containing saline 2, best seen in FIG. 8. Operation of such a system is described in U.S. Pat. No. 3,675,891, hereby incorporated by reference. Once the system has been completely filled with sterile saline solution 2, stopcock 52 is closed so as to form a static fluid column through tubing 16 and 12 which terminates in the fluid filled chamber 56. The static fluid column is then used to mechanically transmit the fluid pulses which are generated by the pumping action of the heart and which thus represent the patient's hemodynamic pressure.

As best shown in FIG. 2, housing 36 is typically constructed of medical grade plastic so as to be very lightweight and disposable. Advantageously, this makes the transducer apparatus 10 more easy to work with in setting up the electromanometry system and also in transporting the patient to or from surgery or the like. Moreover, the proximal half 39 of the transducer housing 36 is preferably constructed of a transparent plastic so as to permit visual inspection of the interior chamber 56. The use of a transparent plastic permits visual inspection for the purpose of determining whether any air bubbles are entrapped within the interior chamber 56. It is important that all of the air bubbles be completely removed from the static fluid column because air bubbles are compressible and hence tend to degrade and distort the mechanical fluid pulses transmitted through the static fluid column.

As best shown in FIG. 3, the distal half 38 of transducer housing 36 is generally cylindrical in shape and surrounds a plurality of connector pins 40 which in turn are electrically connected to the pressure sensing element 66 which is diffused onto a semiconductor substrate 66A which is used to transform the mechanical pulses of fluid into one or more parameters of a corresponding electronic signal. As shown best in FIG. 2, rib 64 is formed longitudinally along the inside surface of the distal half 38 of housing 36. Rib 64 is positioned so as to correspond with a small, raised bump 68 formed on the outer periphery of the ring 48. The rib 64 engages a corresponding slot (not shown) in socket 78 so that each connector pin 40 will be properly aligned with the corresponding holes (not shown) of socket 78. The raised bump 68 aids in ascertaining alignment of the slot (not shown) of socket 78 with rib 64.

As more fully described below, the pressure sensing element 66 of transducer apparatus 10 consists of a thin diaphragm piezoresistive strain gauge in the form of a resistive bridge network 69 diffused onto a semiconductor substrate 66A. As shown best in FIGS. 3 and 4, the connector pins 40 are attached to a metal base 58 on which is mounted a small semiconductor substrate 66A. Pins 40 are connected by very small (almost microscopic) wires 62 at the ends thereof which protrude through the metal base 58 in close proximity to the substrate 66. The outer periphery 57 of the metal base 58 is preferably slightly overlapped by the flange 51 such that the periphery 57 of base 58 is in sealing contact with the interior surface 67 of the housing 36.

The semiconductor substrate 66A, which is typically very small (i.e., on the order of 3.5 mm by 4.0 mm by 0.4 mm) has a plurality of resistive elements diffused onto the substrate by means of conventional semiconductor technology. The schematic diagram for the resistive elements is a bridge network 69, as shown best in FIG. 5. The resistive bridge network 60 consists of resistors R1–R4 which are configurated in the form of a Wheatstone bridge. As the mechanical fluid pulses are applied to the pressure sensing element 66 diffused onto a semiconductor substrate 66A, the pressure sensing element 66 acts like a conventional strain gauge. Each fluid pulse causes the value of one or more of the resistive elements R1–R4 to change. These respective changes in the value of resistors R1–R4 cause an imbalance in the resistive bridge 69 which may be detected at terminals 73–74 and which form the parameters for the electronic signals which correspond to the mechanical fluid pulses. Thus, mechanical fluid pulses are transformed by the transducer apparatus 10 into corresponding electronic signals, which may be observed on monitor 32.

Figure 4:
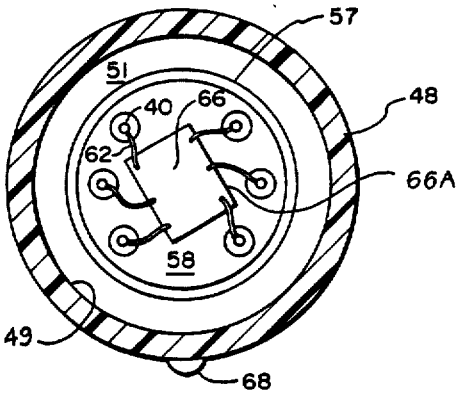
FIG. 4 is a sectional end view taken along lines 4—4 of the disposable pressure transducer of FIG. 2.

With further reference to FIGS. 3 and 4, it will be seen that the semiconductor substrate 66A is positioned at the distal end of interior chamber 56 so as to be in fluid communication with the static fluid column of saline solution 2. A nonconductive gel 60 is spread over the top of the substrate 66A and the base member 58 on which the substrate 66A is mounted. The nonconductive gel 60 completely covers the base 58 and substrate 66A so as to electrically isolate those components from the sterile saline solution used to fill the remaining portion of the interior chamber 56. Importantly, the nonconductive gel 60 must be capable of transmitting the mechanical pulses of fluid to the semiconductor substrate 66A without seriously degrading the quantitative parameters of magnitude and time which characterize the fluid pulses.

In the presently preferred embodiment, the nonconductive gel may be, for example, Dow Corning product no. Q3-6527A. The pressure sensing element 66 which is formed by the resistive bridge network 69 (see FIG. 5) diffused onto the semiconductor substrate 66A is a conventional semiconductor transducer element manufactured by Foxboro/I.C.T., Inc. of San Jose, Calif., and typically provides a 5 micro-volts per volt per millimeter of mercury of input pressure.

Figure 7:
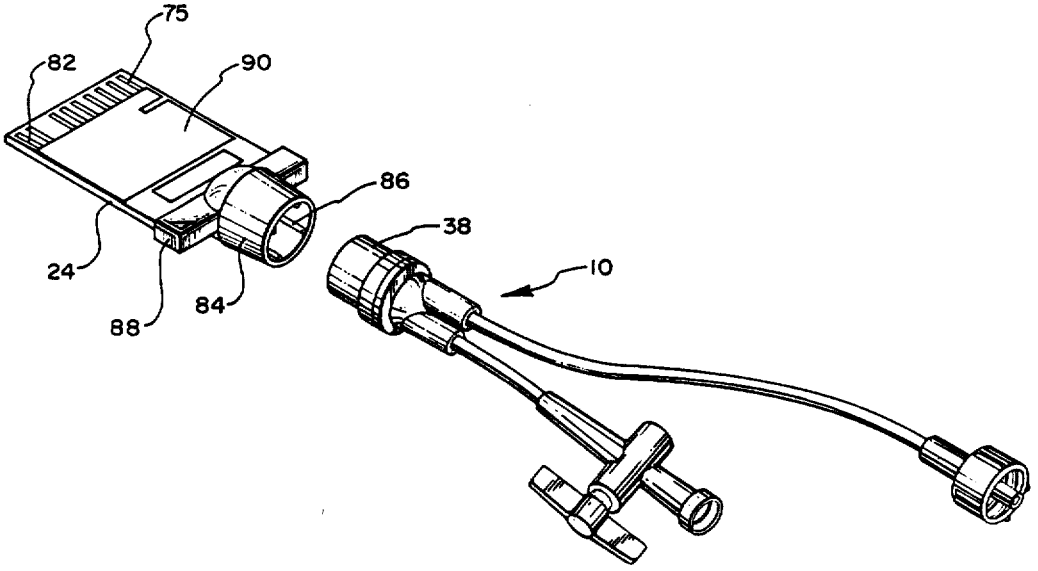
FIG. 7 is a perspective view illustrating the manner in which the disposable transducer and calibration card of FIG. 1 may be joined together for purposes of packaging.

Typically, it is not possible to manufacture the semiconductor substrate 66A in large quantities without having some variation in the values of the resistors R1–R4 which form the resistive bridge network. Accordingly, it is necessary to calibrate the resistors R1–R4 by some means prior to using the resistive bridge network 69 as the pressure sensing element 66 of an electromanometry system. For this purpose, an additional semiconductor substrate is provided on a disposable calibration card 24, shown best in FIGS. 1 and 7. Card 24 has a plurality of resistors which are diffused onto the card and which are used to calibrate the resistors R1–R4 of the resistive bridge network 69 contained on substrate 66A.

Figure 5:
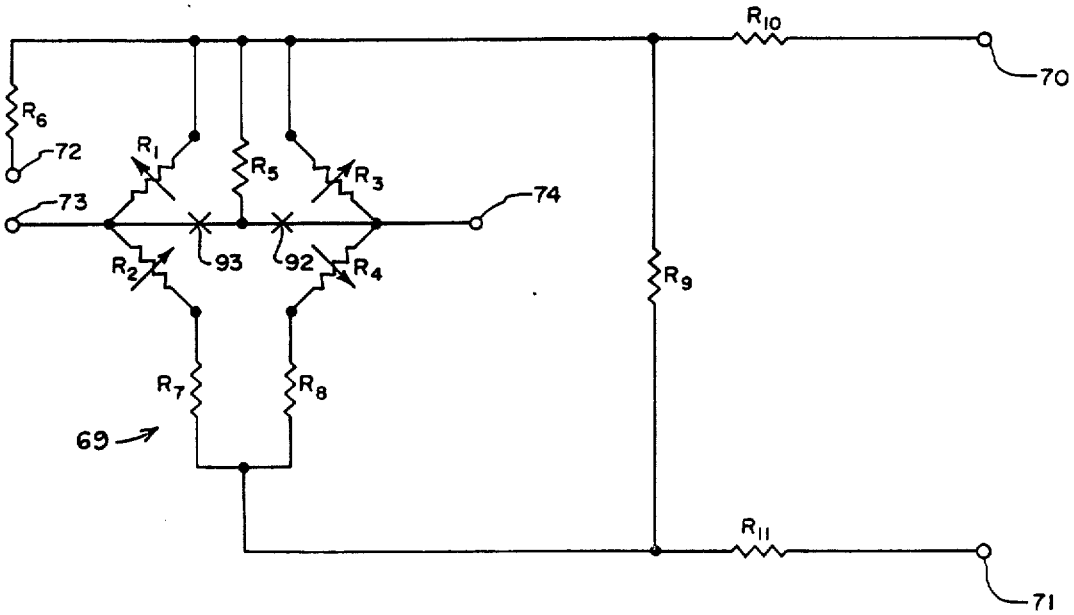
FIG. 5 is an electrical schematic diagram of the calibration resistors and the resistive bridge network of the pressure sensing element of the disposable pressure transducer of FIG. 1.
Figure 6:
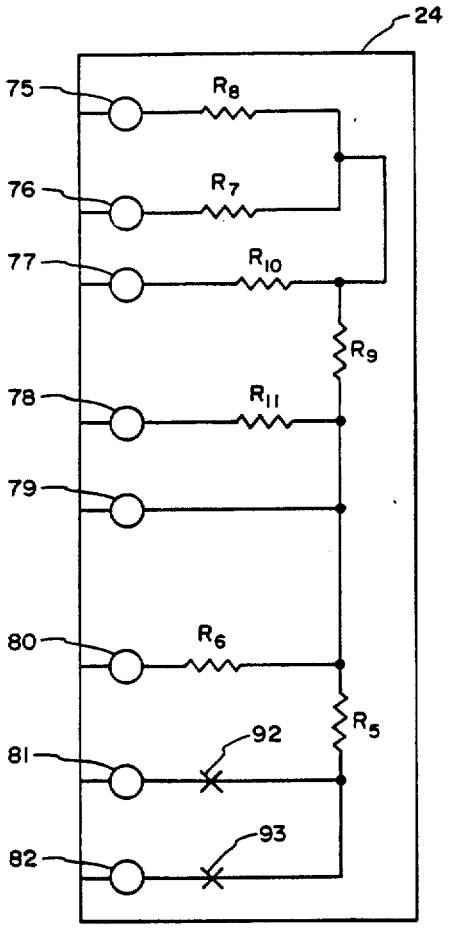
FIG. 6 is a schematic diagram of the calibration card of FIG. 1.

As schematically illustrated in FIG. 6, the disposable calibration card 24 has a plurality of resistors R5–R11 diffused onto the semiconductor substrate of card 24. The resistors are connected by a series of terminals 75–82 to the resistive bridge network 69 formed by the resistors R1–R4 (see FIG. 5) and also to an interface circuit (see FIG. 9) through which the corresponding electronic signals are input to the monitor 32. As schematically illustrated in FIG. 5, resistor R5 is connected in parallel across resistors R1 and R3 of the bridge. Resistors R7 and R8 are connected in series with resistors R2 and R4, respectively. Resistor R9 is connected in parallel across the resistive bridge network 69, series resistors R7–R8, and resistors R6, R10 and R11 which are connected in series with the terminals 72, 70 and 71, respectively. By way of example, resistor R5 is typically between 50k to 500k ohms±1%, with a maximum power rating of one milliwatt. Resistor R6 is typically between 100k to 500k ohms±0.5%, and is rated at one milliwatt. Resistors R7 and R8 are 100 to 150 ohms±1%, and are rated at 0.1 milliwatt. R9 is typically 1k to 20k ohms±1%, ranging from 80 milliwatts at 1k ohm to 8 milliwatts at 20k ohms. Resistors R10 and R11 are 4k to 25k ohms±0.5%, and are rated at approximately 30 milliwatts.

As schematically illustrated in FIG. 6, a pair of contacts 92–93 are also provided on the disposable calibration card 24. One of the contacts is open, while the other is closed. In the illustrated embodiment, the disposable calibration card 24 on which the calibration resistors are diffused is typically 1 inch by 1¼ inches by 0.0625 inch. As shown best in FIG. 7, the card is covered by a protective cover of plastic or other suitable material as at 90. The card is bonded or otherwise attached to a rectangular base 88 which includes a cylindrical mounting 84 that is adapted to fit over the distal half 38 of housing 36 of the transducer apparatus 10. Cylindrical mounting 84 has several ribs 86 which are designed to frictionally engage the corresponding cylindrical end 38 of the transducer apparatus 10.

Each disposable transducer 10 which is manufactured may thus also be provided with a unique calibration card 24 which is especially configured so as to calibrate that particular transducer. For purposes of packaging the device the disposable calibration card 24 can be slipped onto the end of the transducer apparatus 10 so that the two components are not separated. In the alternative, the calibration resistors could be formed directly on a thin film substrate and contained within the transducer housing 36. In either case, it is possible to insure that each transducer apparatus 10 will not become separated from the particular calibration resistors which are designed to be used with that particular transducer.

When use of the transducer apparatus 10 is completed in connection with its use for a particular patient, both the transducer apparatus 10 and the calibration card 24 may be conveniently disposed of so as to eliminate potential cross contamination which might otherwise occur by virtue of using the transducer apparatus 10 in connection with any other patient.

While the present invention has been described with reference to the presently preferred embodiment illustrated in the drawings herein, the invention may be embodied in other specific forms without departing from its spirit or essential characteristics. Thus, the described embodiments are to be considered in all respects only as illustrative and not restrictive. The scope of the invention is, therefore, indicated by the appended claims rather than by the foregoing description and all changes which come within the meaning and range of equivalency of the claims are to be embraced within their scope.

What is claimed is:

1. In an electromanometry system for monitoring and recording hemodynamic pressures, a disposable transducer apparatus, said electromanometry system including a catheter coupled through tubing to a source of sterile liquid which is used to fill the tubing and cathether and through which said hemodynamic pressures are mechanically transmitted, said apparatus comprising:

a disposable housing constructed of light weight plastic material, said housing having a transparent chamber with an inlet and outlet, said chamber being connected at said inlet to said tubing;

valve means connected to the outlet of said chamber for selectively venting the interior of said chamber to the ambient atmosphere;

a pressure sensing element mounted at one end of said chamber; said pressure sensing element comprising a thin-diaphragm piezoresistive strain gauge in the form of a resistive bridge network diffused onto a semiconductor substrate;

a nonconductive gel-like substance contained within said chamber, said nonconductive gel-like substance completely covering said pressure sensing element and transmitting said hemodynamic pressures from said sterile liquid to said pressure sensing element; and a plurality of disposable calibration resistors electrically connected to said resistive bridge network, said resistors being formed on a semiconductor *or thin film* substrate.

2. The system of claim 1 and further comprising;

a continuous flow valve means for providing a steady supply of a desired quantity of sterile liquid to said catheter;

tubing fast flush means incorporated in said continuous flow valve means for selectively providing an increased quantity of said sterile liquid through said tubing to said catheter.

3. The system of claim 2 wherein said disposable calibration [card further comprises] *resistors are provided on a disposable calibration card, said card further comprising* means for attaching said disposable calibration card to said disposable transducer such that both said disposable calibration card and the disposable transducer may be packaged together to prevent them from being separated one from the other until such time as it is desired to use the disposable transducer.

4. In an electromanometry system for monitoring and recording hemodynamic pressures, a disposable transducer apparatus, said electromanometry system including a catheter coupled through tubing to a source of sterile liquid which is used to fill the tubing and catheter and through which said hemodynamic pressures are mechanically transmitted, said apparatus comprising:

a housing, said housing having a chamber and in inlet to said chamber placing the interior of the chamber in fluid communication with the tubing;

a pressure sensing element operatively positioned in said chamber, said pressure sensing element comprising means for converting the said mechanically transmitted hemodynamic pressures to an electronic signal;

means for calibrating said pressure sensing element comprising a plurality of resistors diffused onto a semiconductor *or thin film* substrate;

means for electrically connecting said pressure sensing element to said means for calibrating the pressure sensing element; and electrical isolation means disposed in said chamber for electrically isolating said pressure sensing element from said sterile liquid without inhibiting the mechanical transmission of said hemodynamic pressures through said sterile liquid and through said electrical isolation means to said pressure sensing element.

5. The system of claim 4 wherein said plurality of resistors are formed on a semiconductor substrate which is contained on a disposable calibration card.

6. The system of claim 5 wherein said disposable calibration card comprises means for attaching said card to said housing such that said card and said disposable transducer apparatus may be packaged together as a single unit until such time as the disposable transducer apparatus is removed from its package for use in an electromanometry system.

7. The system of claim 5 wherein said means for electrically connecting said pressure sensing element to said means for calibrating the pressure sensing element comprises:

a length of electrical cable connected at one end to said pressure sensing element; and an electrical socket connected at the other end of said length of electrical cable, said socket having a generally flat configuration and having a slot for receiving in electrical engagement a portion of said disposable calibration card.

8. In an electromanometry system for monitoring and recording hemodynamic pressures, a disposable transducer apparatus said electromanometry system including a catheter coupled through tubing to a source of sterile liquid which is used to fill the tubing and catheter through which said hemodynamic pressures are mechanically transmitted, said apparatus comprising:

a housing, said housing having a chamber and an inlet to said chamber placing the interior of the chamber in fluid communication with said tubing;

a pressure sensing element mounted at one end of said chamber, said pressure sensing element comprising means for converting the said mechanically transmitted hemodynamic pressures to at least one parameter of an electronic signal;

a calibration means for electronically calibrating said pressure sensing element, said calibration means being electrically connected to said pressure sensing element and further comprising a plurality of resistors diffused onto a semiconductor *or thin film* substrate;

electrical isolation means disposed in said chamber for electrically isolating said pressure sensing element from said sterile liquid, said electrical isolation means mechanically transmitting said hemodynamic pressures from said sterile liquid to said pressure sensing element.

9. The system of claim 8 wherein said semiconductor substrate onto which said plurality of resistors are diffused is formed on a disposable calibration card which is separate from said disposable transducer apparatus.

* * * * *